(12) United States Patent
Wang et al.

(10) Patent No.: US 8,421,903 B2
(45) Date of Patent: Apr. 16, 2013

(54) STAGGERED CONTACT IMAGE SENSOR IMAGING SYSTEM

(75) Inventors: Shaohong Wang, Belle Mead, NJ (US); Carlos Barnes Gonzalez, Princeton, NJ (US)

(73) Assignee: Abbott Laboratories, Abbott Park, IL (US)

( * ) Notice: Subject to any disclaimer, the term of this patent is extended or adjusted under 35 U.S.C. 154(b) by 357 days.

(21) Appl. No.: 12/776,797

(22) Filed: May 10, 2010

(65) Prior Publication Data

US 2011/0273547 A1    Nov. 10, 2011

(51) Int. Cl.
*H04N 5/225*    (2006.01)

(52) U.S. Cl.
USPC ............ 348/340; 348/180; 348/187; 348/189

(58) Field of Classification Search .................. 348/180, 348/187, 189, 340
See application file for complete search history.

(56) References Cited

U.S. PATENT DOCUMENTS

| | | | |
|---|---|---|---|
| 5,450,157 | A | 9/1995 | Rees |
| 6,473,238 | B1 * | 10/2002 | Daniell .......... 359/622 |
| 6,563,647 | B2 | 5/2003 | Fukuzawa |
| 6,597,512 | B2 | 7/2003 | Toyama |
| 6,866,823 | B2 | 3/2005 | Wardlaw |
| 2003/0112523 | A1 * | 6/2003 | Daniell .......... 359/626 |
| 2004/0032581 | A1 | 2/2004 | Nikoonahad et al. |
| 2007/0153370 | A1 | 7/2007 | Olszak et al. |
| 2009/0101799 | A1 | 4/2009 | Kochi |
| 2009/0237665 | A1 | 9/2009 | Wardlaw et al. |
| 2011/0032369 | A1 * | 2/2011 | Ludwig .......... 348/218.1 |
| 2011/0122308 | A1 * | 5/2011 | Duparre .......... 348/340 |
| 2011/0254916 | A1 * | 10/2011 | Fan et al. .......... 348/41 |

FOREIGN PATENT DOCUMENTS

EP    0871052    10/1998

OTHER PUBLICATIONS

"CCD Versus CIS: Does the Type of Wide-Format Scanning Technology Matter?", Stanley Adams Group 2008, Dec. 12, 2008, www.stanleyadamsgroup.com/Technologies/.../Does%20wide-format%20Scanning%20Technology%20Matter%20ver2.pdf.
"SELFOC Lens Array (SLA)", NSG Europe, Mar. 11, 2001, http://nsgeurope.com/sla/shtml.
Cui et al., "Lenless High-Resolution On-Chip Optofluidic Microscopes for Caenorhabditis Elegans and Cell Imaging", PNAS, vol. 105, No. 31, Aug. 5, 2008.

* cited by examiner

*Primary Examiner* — Phuoc Nguyen
(74) *Attorney, Agent, or Firm* — O'Shea Getz P.C.

(57) ABSTRACT

A method and an apparatus for imaging a biologic sample is provided. The apparatus includes at least one light source, at least one lens array, at least one image detector, a positioning system, and an image processor. The lens array has a plurality of lengthwise extending rows, which rows are successively arranged in a widthwise direction. Each row has a plurality of micro lenses, with each micro lens having a resolution field. Each micro lens is adapted to receive light from the illuminated region of the sample and to produce a beam of light. Each row includes a first micro lens and the first micro lens in each successive row is offset from the first micro lens in the previous row by a predetermined amount extending in the lengthwise direction. The offset between successive rows aligns the resolution fields of the micro lenses to collectively create a continuous resolution field across the length of the lens array. The positioning system moves the lens array and image detector relative to the sample, or vice versa, or both. The image processor produces an image signal indicative of the illuminated region of the sample produced from data signals from the image detector.

23 Claims, 8 Drawing Sheets

STAGGERED CONTACT IMAGE SENSOR IMAGING SYSTEM

BACKGROUND OF THE INVENTION

1. Technical Field

This disclosure relates generally to contact image sensors and, more particularly, to a contact image sensor system having one or more staggered rod lens arrays.

2. Background Information

Contact image sensors (also referred to as a "CIS") are widely used for optically scanning samples due to their relatively low costs. A typical CIS includes a rod lens array having a plurality of cylindrical micro lenses, and a detector array having a plurality of charge-coupled devices (also referred to as a "CCD"). Each micro lens is configured to direct light from a target to be imaged (e.g., a biological sample, which target is referred to hereinafter as a "sample") to a respective one of the CCDs, producing one pixel of an image of the sample. Collectively, the pixels from each of the CCDs are compiled together to produce the image of the scanned region of the sample.

Typically, the prior art image sensors have a resolution that depends upon the distance between the rod lens array and the sample. For example, to enhance the resolution of the CIS to a sub-micron level, the distance between the rod lens array and the sample must be reduced to a sub-micron level. FIG. 4 illustrates the typical relationship between working distance and resolution in prior art CISs. As can be seen from the graph, there are limitations regarding the resolution that can be attained using prior art CISs. Even in those applications where an acceptable high resolution can be reached, the working distance is such that it is quite difficult to position the sample being imaged.

SUMMARY OF THE DISCLOSURE

According to an aspect of the present invention, an apparatus for imaging a biologic sample is provided that includes at least one light source, at least one lens array, at least one image detector, a positioning system, and an image processor. The light source is adapted to selectively illuminate a region of the sample. The lens array has a plurality of lengthwise extending rows, which rows are successively arranged in a widthwise direction. Each row has a plurality of micro lenses, with each micro lens having a resolution field. Each micro lens is adapted to receive light from the illuminated region of the sample and to produce a beam of light. Each row includes a first micro lens and the first micro lens in each successive row is offset from the first micro lens in the previous row by a predetermined amount extending in the lengthwise direction. The offset between successive rows aligns the resolution fields of the plurality of micro lenses to collectively create a continuous resolution field across the length of the lens array. The image detector is adapted to receive light beams from the lens array and provide data signals representative of the received light beams. The positioning system is adapted to move the lens array and image detector relative to the sample, or vice versa, or both. The image processor is adapted to produce an image signal indicative of the illuminated region of the sample produced from the data signals.

According to another aspect of the present invention a staggered lens array is provided that includes a plurality of lengthwise extending rows, which rows are successively arranged in a widthwise direction. Each row has a plurality of micro lenses, with each micro lens having a resolution field of "n" microns. Each micro lens is adapted to receive light and produce a beam of light. Each row includes a first lens and the first lens in each successive row is offset from the first lens in the previous row by a predetermined amount extending in the lengthwise direction. The offset between successive rows aligns the resolution fields of the plurality of micro lenses to collectively create a continuous resolution field across the length of the lens array.

According to another aspect of the present invention, a method of imaging a sample is provided. The method includes the steps of: a) providing an imaging unit having a light source, a lens array, and an image detector, wherein the lens array has a width, a length, and a plurality of lengthwise extending rows, which rows are successively arranged in a widthwise direction, and each row having a plurality of micro lenses each having a resolution field, and each adapted to receive light and produce a beam of light, wherein each row includes a first micro lens and the first micro lens in each successive row is offset from the first micro lens in the previous row by a predetermined amount extending in the lengthwise direction; b) selectively illuminating the sample, such that light exiting the sample is received by the lens array and passed to the image detector, which image detector produces data signals representative of the sample from the received light; c) moving one or both of the imaging unit and sample relative to the other such that substantially all of the sample is illuminated; and d) processing the data signals to produce an image of the sample.

The foregoing features and advantages and the operation of the invention will become more apparent in light of the following description of the best mode for carrying out the invention and the accompanying drawings.

DETAILED DESCRIPTION OF THE INVENTION

Figure 1:
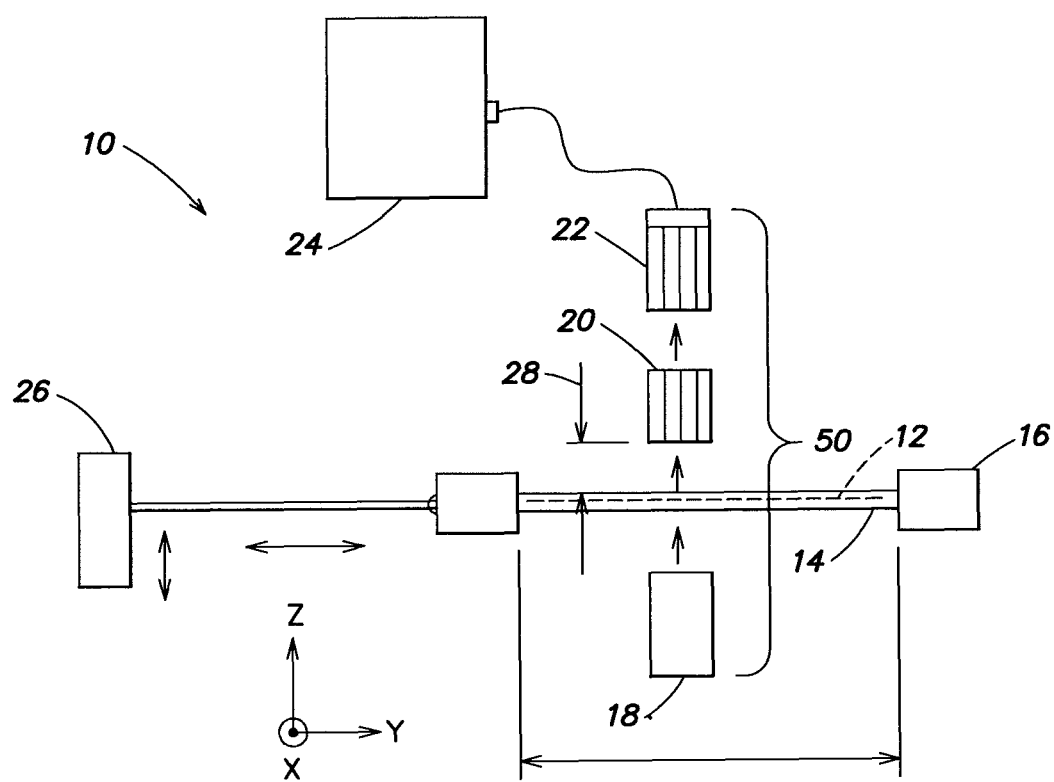
FIG. 1 is a diagrammatic illustration of present invention imaging system.

Referring to FIG. 1, a staggered contact image sensor (hereinafter "staggered CIS") imaging system 10 is diagrammatically shown for microscopically imaging a sample 12 along a scanning direction. A biological or chemical specimen having one or more analytes disposed within a sample chamber 14 is an example of a target (referred to hereinafter as a "sample") that can be imaged using the present staggered CIS imaging system 10. For purposes of describing the present staggered CIS imaging system 10, the sample 12 is described as quiescently residing within a chamber 14 and both the chamber 14 and the sample 12 have a width that extends substantially parallel to the scanning direction of the staggered CIS imaging system 10 (e.g., along a "Y" axis), and a length that extends substantially perpendicular to the scanning direction of the staggered CIS imaging system 10 (e.g., along an "X" axis that extends in and out of the page containing FIG. 1). The present invention system 10 and method can be used with a variety of different sample cartridges 16. An example of an acceptable sample cartridge is disclosed in U.S. Patent Appln. Ser. No. 61/268,955, which is hereby incorporated by reference in its entirety. U.S. Patent Publication No. 2009/0237665 (U.S. patent application Ser. No. 12/408,479) to Wardlaw et al., which is also hereby incorporated by reference in its entirety, describes an apparatus and techniques that facilitate focusing of an imaging system (e.g., along a "Z" axis). The aforesaid apparatus and techniques can be used with the present imaging system 10.

The present staggered CIS imaging system 10 includes a light source 18, a staggered rod lens array 20 (hereinafter the "lens array"), an image detector 22, an image processor 24, and a positioning system 26. In some embodiments, the light source 18 is disposed on a first side of the sample 12 (e.g., vertically below the sample 12) and the lens array 20 and the image detector 22 are disposed on the opposite side of the sample 12. In this configuration, the light source 18 transmits light through the sample 12, and the lens array 20 and image detector 22 receive the light transmitted through the sample 12. In alternative embodiments, the light source 18, lens array 20, and image detector 22 are disposed elsewhere, including embodiments where the light is directed toward the sample 12 by mirrors, etc. In still other embodiments, more than one light source 18 can be utilized, disposed at different positions relative to the sample chamber 14. The lens array 20 is disposed a distance 28 from the illuminated region of the sample 12. The distance is referred to as the "working distance", and typically represents the distance between the end faces of the lens 30 within the array 20 and the surface of the sample 12 being imaged. A working distance for a system operable to image a whole blood sample is typically within the range of 0.1 mm to 0.2 mm. As used herein, the "surface" of the sample 12 being imaged refers to a Z-axis plane within the sample 12 where the sample 12 is acceptably focused for the tests at hand. Each lens 30 within the lens array 20 is configured to direct light transmitted through (or emanating from) the illuminated region to the image detector 22. The image processor 24 is connected to and in communication with the image detector 22. The positioning system 26 is configured to selectively move portions of the staggered CIS imaging system 10 relative to the sample 12, or vice versa, such that different regions of the sample 12 can be illuminated and imaged, and for focus purposes.

The light source 18 may be a single broadband light source operable to produce light along multiple wavelengths, or a plurality of light sources, each producing light at a particular wavelength. In those applications where a multiple wavelength light source 18 is used, one or more light filters (not shown) may be used to selectively allow particular wavelengths for certain applications. An example of how light filters may be utilized with a multiple wavelength light source is disclosed in U.S. Pat. No. 6,866,823 to Wardlaw, which is hereby incorporated by reference in its entirety. The light source 18 selectively produces light at wavelengths within a particular range (e.g., between approximately 340 nm to 670 nm) broad enough to be useful for a plurality of imaging techniques. An example of an acceptable light source 18 is one that includes a plurality of light emitting diodes (i.e., "LEDs"). Other acceptable light sources 18 include high-pressure mercury or xenon lights, zenon arc lamps, tungsten halogen lamps, pulsatile light sources, etc. The light source 18 is not limited to producing light in a transmittance mode; e.g., it can also be used to cause one or more colorants (e.g., dyes, stains, etc.) within the sample 12 to produce a fluorescent emission. The light source 18 is configured to illuminate a region of the sample 12. In some instances, the illuminated region may be a substantially continuous line of light (sometimes referred to as a "light line") that illuminates a segment of the sample 12. The light line may be formed, or made more uniform, by passing the light through a diffuser or light pipe.

Figures 2, 3:
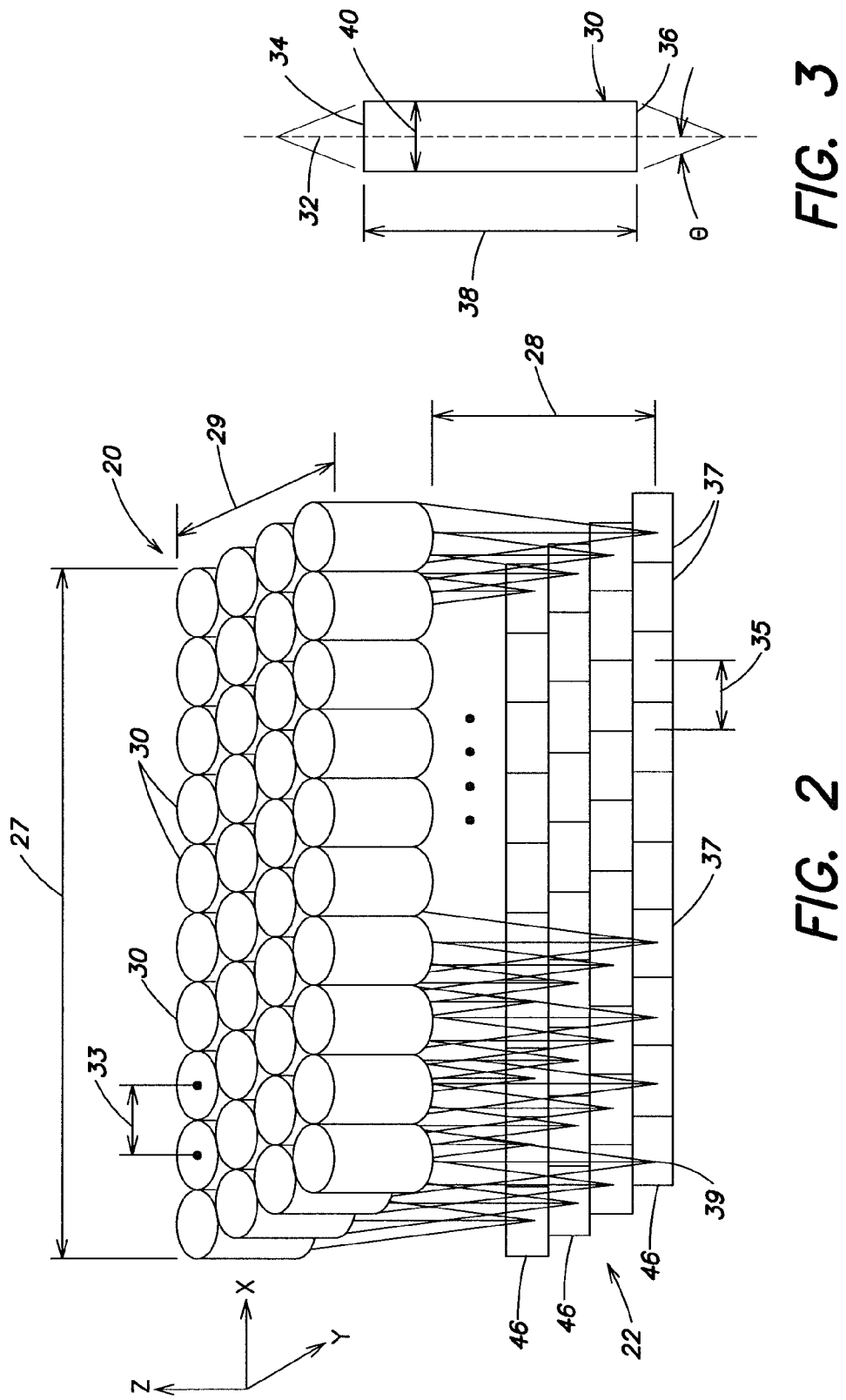
FIG. 2 is a perspective diagrammatic illustration of a four row embodiment of a present invention staggered rod lens array and an image detector.
FIG. 3 is a diagrammatic illustration of a cylindrical micro lens.

Referring to FIGS. 2, 3, 6, and 7, the lens array 20 includes a length 27, a width 29, a plurality of micro lens 30 arranged in a plurality of rows 31. Each micro lens 30 (see FIG. 3) has an optical axis 32, a light reception surface 34, a light emitting surface 36, a length 38, a diameter 40, and an optical resolution field 42 (see FIGS. 6 and 7). The length 38 of each micro lens 30 extends along the optical axis 32 between the light reception surface 34 and the light emitting surface 36. The optical resolution field 42 of each rod micro lens 30 is a dimensional characteristic of the lens 30 that refers to an area of the illuminated region that can be resolved (i.e., non-blurred) into a detailed image, based on the angular aperture of the lens 30 and the working distance between the lens 30 and the chamber plane. The angular aperture of the lens 30 refers to the range of angles over which light can enter or exit the lens 30. FIG. 3 diagrammatically illustrates the range of angles of a lens 30 in terms of the half angle theta ($\theta$). The numerical aperture ("NA") of a lens is a dimensionless number that characterizes the range of angles over which the lens can accept or emit light, and can be described mathematically as:

$$NA = n \sin \theta.$$

Figure 4:
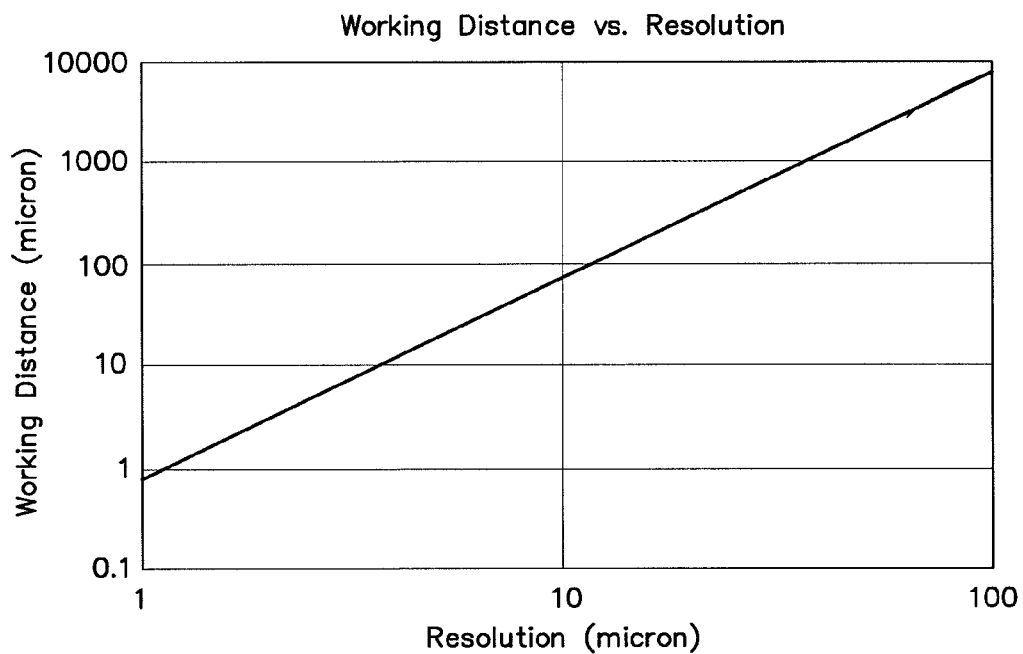
FIG. 4 is a graph of working distance versus resolution for micro lenses within a prior art contact image sensor.

The graph shown in FIG. 4 illustrates the relationship between working distance 28 and lens resolution of a prior art contact image sensor.

Figure 5:
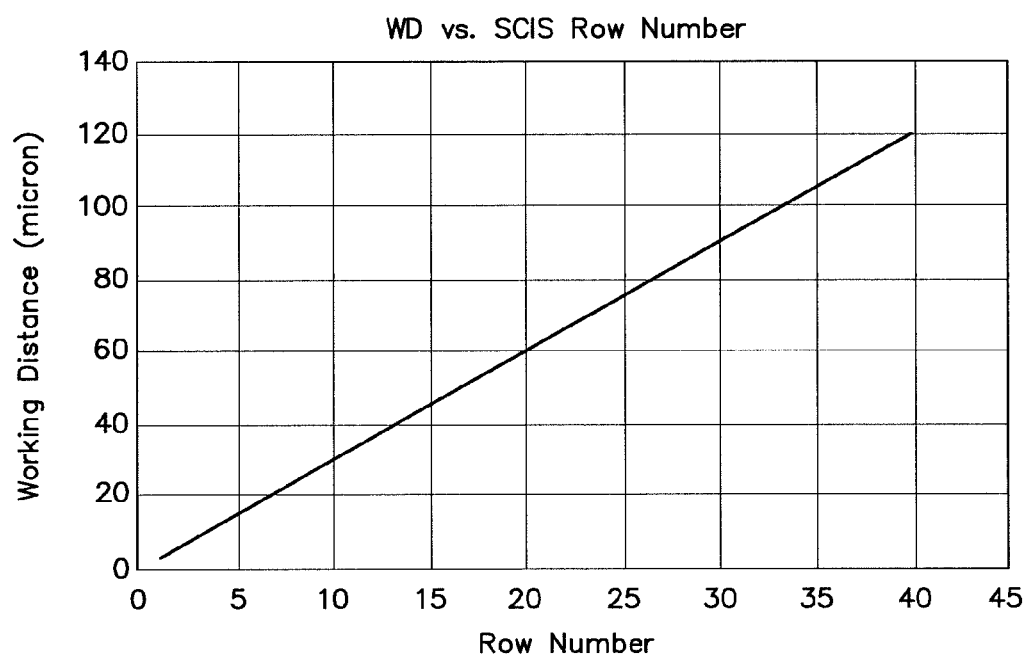
FIG. 5 is a graph of working distance versus number of rows within a present invention lens array.

The number of rows 31 included in the present invention lens array 20 is chosen based on a desired resolution field 42 of each lens 30 within the array 20, a desired working distance between the rod micro lenses 30 within the array 20 and the sample plane, and the diameter of each lens 30 within the array 20. The graph shown in FIG. 5 illustrates the relationship between the number of rows 31 within a present invention staggered lens array 20, and the working distance possible with such an array 20. As will be described below, the lens array 20 configuration within the present invention makes it possible to provide a resolution field 42 that is fine while maintaining a large working distance, relative to that possible with conventional CISs. Within each row 31 of micro lenses 30 in the array, "N" number of lenses 30 (where "N" is an integer) are disposed along a lengthwise extending line (i.e., along the "X" axis). The pitch 33 within a row 31 is defined as the lengthwise distance between the optical axes 32 of adjacent micro lenses 30 in the same row 31. In the embodiment shown in FIG. 2, there are four rows 31, each having ten rod micro lenses 30 (i.e., N=10), for a total of forty rod micro lenses 30 within the array 20. In the embodiment shown in FIG. 5, there are five rows 31, each having eight rod micro lenses 30 (i.e., N=8), for a total of forty rod micro lenses 30 within the array 20.

Figure 6:
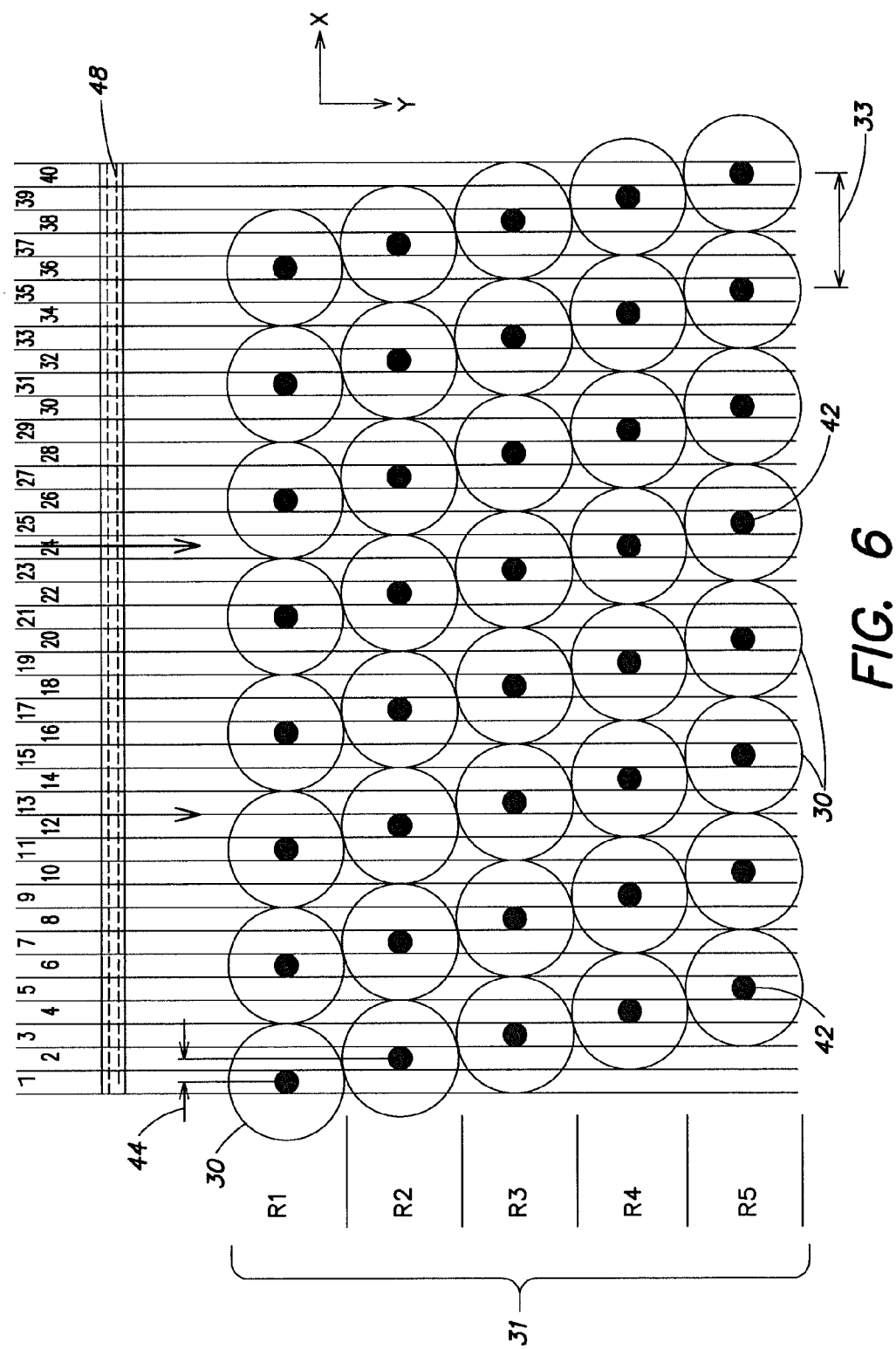
FIG. 6 is a diagrammatic illustration of a five row embodiment of a present invention staggered lens array, having a row to row offset of one micron.
Figure 7:
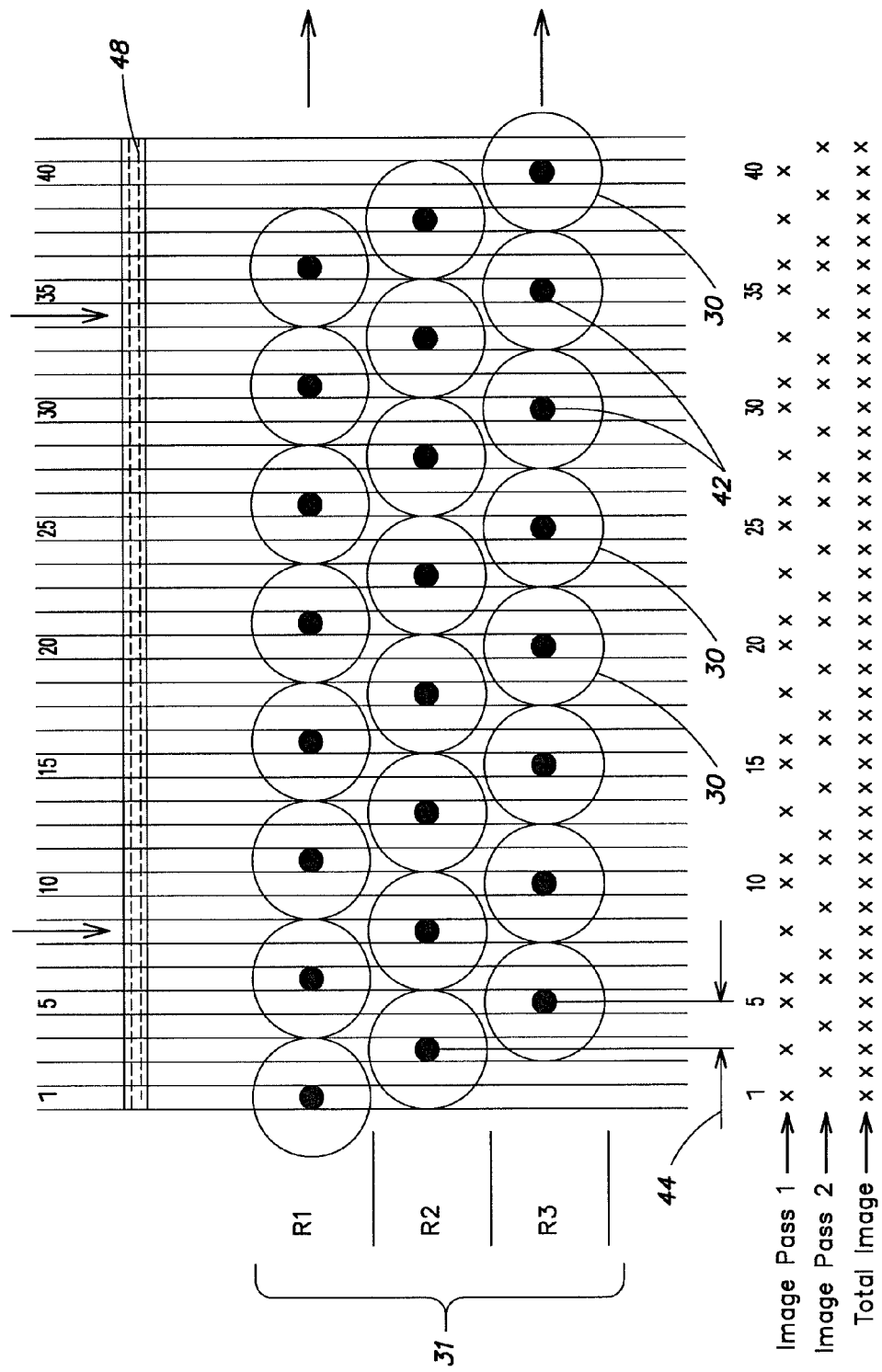
FIG. 7 is a diagrammatic illustration of a three row embodiment of a present invention staggered lens array, having a row to row offset of two microns.

Each row 31 of micro lens 30 is "staggered" (which may also be described as "shifted") relative to adjacent rows 31 within the array 20 in a lengthwise direction by an amount that is referred to as an offset 44 (see FIGS. 6 and 7). Each row 31 is staggered in the same direction. For example, in an embodiment wherein the amount of stagger between successive rows is uniformly equal to "x" distance, then the first micro lens 30 in the second row is staggered "x" distance from the first micro lens 30 in the first row, and the first micro lens 30 in the third row is staggered "2x" distance from the first micro lens 30 in the first row, etc. The amount of the offset 44 within an array 20 can vary to suit the application. For the biological fluid sample imaging examples provided herein, an offset 44 that is equal to approximately one half to two times the optical resolution field 42 of the micro lens 30 has substantial utility. The lens array 20 embodiment shown in FIG. 6 is shown with five micron (5μ) diameter lenses 30, each having an optical resolution field 42 equal to one micron (1μ). Each successive row 31 within the four row array 20 is offset by one micron in the same direction. The lens array 20 shown in FIG. 6 provides an uninterrupted image resolution in a lengthwise direction when the array 20 is moved relative to the sample 12 in the scanning direction (i.e., in a widthwise direction) an amount substantially equal to the width of the array 20, as will be explained in greater detail below.

The lens array 20 is positionable in alignment with the sample 12, and in particular is selectively alignable with the region of the sample 12 illuminated by the light source 18 during operation of the imaging system 10. In some embodiments of the system 10, the lens array 20 and the light source 18 are in fixed positions relative to one another. As indicated above, the imaging unit 50 (e.g., the light source 18, lens array 20, etc.) can be moved relative to the sample 12 or vice versa. The lens array 20 and the light source 18 are configured relative to one another such that a substantial amount of the light produced by the light source 18 is received by the lens array 20. In a transmittance mode, for example, substantially all of the light passing through the sample 12 is received by the lens array 20. In a fluorescence mode, a useful amount of the light produced by the excitation of the colorant disposed within the sample 12 is received by the lens array 20. The term "useful amount" is used to describe an amount of light sufficient for imaging purposes for the analytical tests at hand. The light received by each lens 30 within the lens array 20 is focused within the respective lens 30 to produce the aforesaid resolution field 42 (e.g., 1μ resolution field).

One of the substantial advantages of the present invention array 20 is that it provides desirable high resolution and allows the use of relatively large diameter lenses 30. The large diameter lens 30 provides the desired resolution at a greater working distance, thereby facilitating the arrangements of optics and sample 12. In many instances, large diameter micro lenses 30 are readily commercially available and cost effective.

Figure 8:
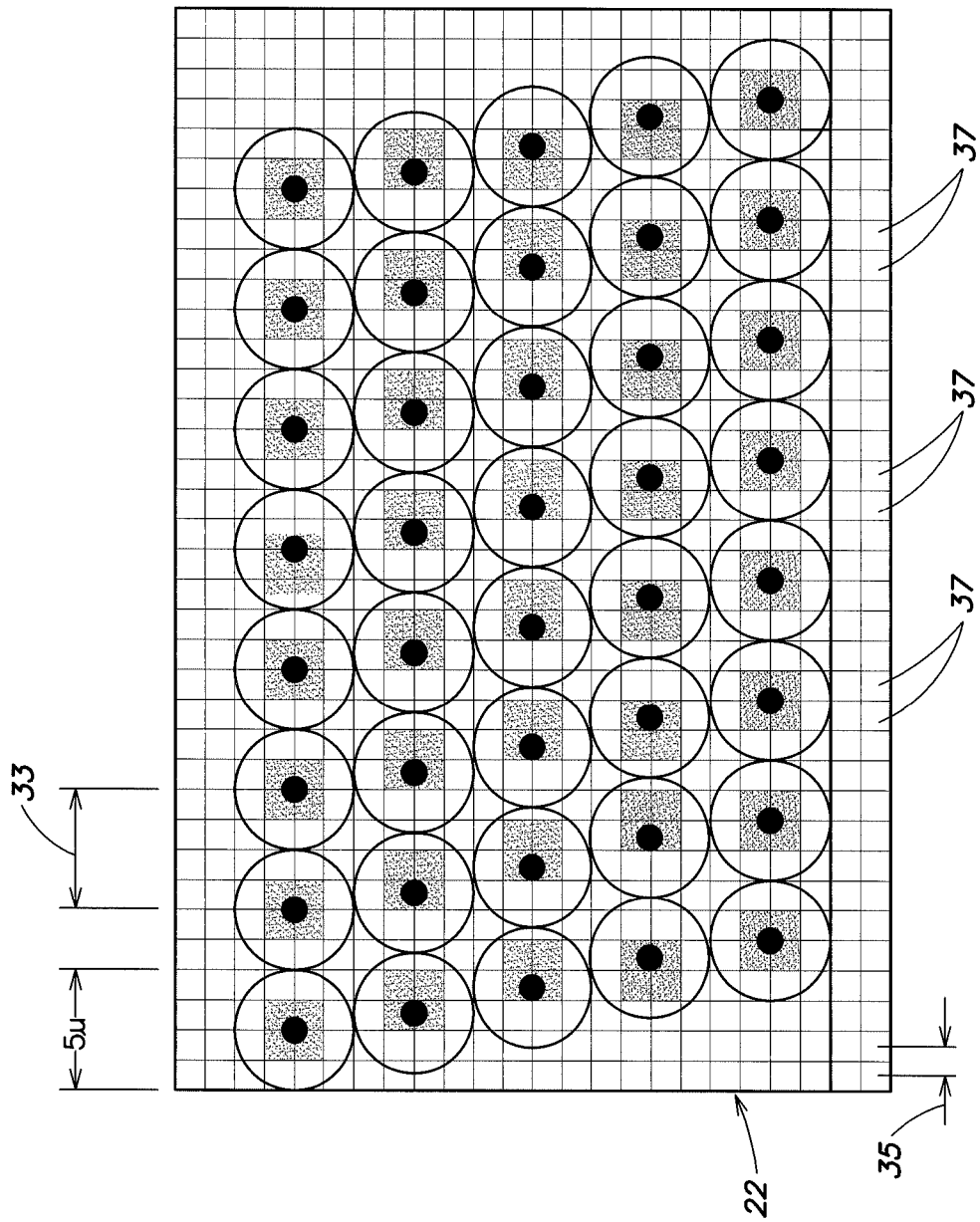
FIG. 8 is a diagrammatic illustration of an image detector with micro lenses superimposed micro lenses.

Referring to FIGS. 1 and 2, the image detector 22 is adapted to receive the focused light directed from the lens array 20 and produce a corresponding data signal. The image detector 22 includes a plurality of image detector elements 37. An example of an acceptable image detector element is a charge-coupled device (hereinafter "CCD") element 37. In an alternate embodiment, the image detector 22 includes image detector elements in the form of complementary metal oxide semiconductor (hereinafter "CMOS") elements. Each CCD (or other image detector 22 component) element 37 is aligned to receive the focused light directed from a particular micro lens 30. For convenience sake, the image detector elements 37 will be described hereinafter as CCD elements 37, although the present invention is not limited to using CCD type elements. In the embodiment shown in FIG. 2, the CCD elements 37 are disposed within a detector array having a plurality of rows 46, which rows 46 are staggered in a manner that mirrors the configuration of the lens array 20. The CCD pitch 35 in the diagrammatic example shown in FIG. 2 is approximately equal to the pitch 33 of the micro lenses 30 within the array 20. Depending upon the specific characteristics of the lens array 20, a 1:1 ratio with the CCD elements 37 can be accomplished using commercially available components or custom designed components. In such arrangements, it is preferable that the beam focus spot 39 produced out of the light emitted surface of each micro lens 30 be a fraction (e.g., ≦50%) of the pitch 35 between CCD elements 37 to prevent crosstalk between adjacent CCD elements. Alternatively, the image detector 22 can have a greater resolution than the lens array 20. For example as shown in FIG. 8, the image detector 22 may comprise an array of CCD elements 37 substantially smaller in size than the micro lenses 30, with a CCD element pitch 35 that is equal or less than 25% of the micro lens pitch 33 within the lens array 20 (depicted as having 5μ micro lenses). In FIG. 8, micro lenses 30 are shown diagrammatically superimposed on the image detector 22 to illustrate the relative sizing and spacing of the micro lenses 30 and the CCD elements 37 within the image detector 22. In such arrangements, the beam intensity focused by each micro lens 30 can be integrated over a number of CCD elements 37 (e.g., over a 2×2 region), and the integration pattern can be obtained by calibration of the imaging system as necessary. The above-described micro lens to CCD element ratio embodiments are examples provided for illustrative purposes. A variety of other ratio embodiments can be used alternatively. In most instances, any micro lens/CCD element configuration that satisfies the following two conditions will be acceptable:

$$\left[\frac{L_p}{\sqrt{2}} - \frac{L_p}{4N}\right] > \frac{L_p}{\sqrt{2}\,N} \quad (1)$$

$$\left[\frac{L_p}{\sqrt{2}} - \frac{L_p}{4N}\right] > 2*r \quad (2)$$

where: "$L_p$" is the micro lens pitch 33, "N" is the ratio between the micro lens pitch 33 and the CCD element pitch 35, and "r" is the radius of the micro lens focus spot 39 on the image dissector 22. The image detector 22 used within the present invention is not, however, limited to these embodiments. CCDs and CMOSs are well known in the art and therefore will not be discussed in further detail.

Figure 9:
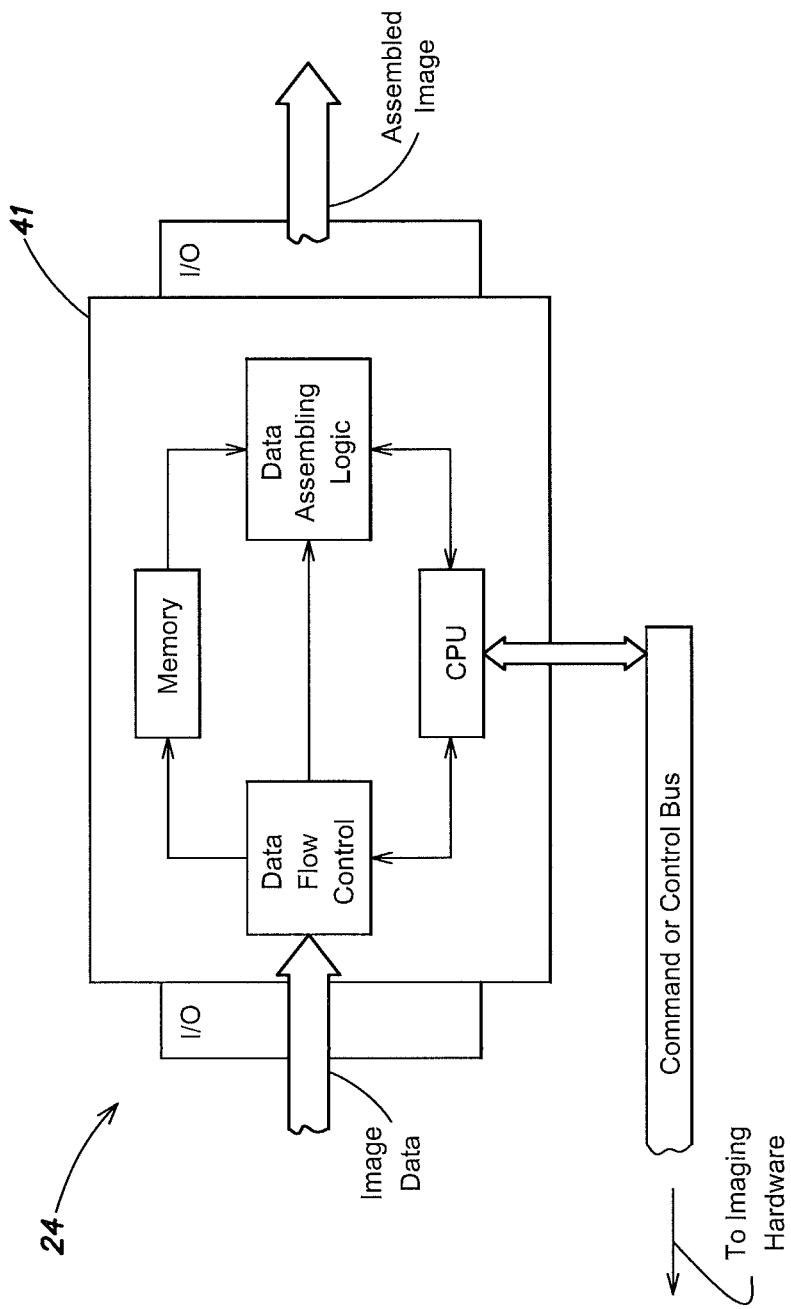
FIG. 9 is a flow diagram illustrating an example of an image processor embodiment.

The image processor 24 is adapted to receive data signals from the image detector 22, and compile signals representative of the illuminated region of the sample 12 which can be used to produce such an image. The functionality of the image processor 24 may be implemented using hardware, software, firmware, or a combination thereof. A person of skill in the art would be able to configure (e.g., program) the image processor 24 to perform the functionality described herein without undue experimentation. In some embodiments, the image processor 24 is further adapted to control and/or synchronize the operation of one or both of the light source 18 and the positioning system 26. FIG. 9 illustrates an example of a image processor 24 configuration. In this example, the image processor 24 includes a field programmable gate array (FPGA) based image assembler 41 having a CPU, memory, a data assembling logic block, and a data flow control block. The FPGA based image assembler accepts signals (e.g., image data signals) from image system components (e.g., image detector 22). Those signals are processed via the CPU, dataflow control block, and data assembling logic block to form the assembled image, which can then be further processed to determine analysis data based on the image, and/or processed for display. Communications between the FPGA based image assembler and other system components (e.g., image detector 22, light source 18, positioning system 26, etc.) can be accomplished through a command/control bus.

The positioning system 26 is adapted to selectively change the position of light source 18, lens array 20, and image detector 22 (collectively referred to hereinafter as an "imaging unit") relative to the sample 12, or vice versa, or both relative to each other. For example, the positioning system 26 is operable to create the relative movement between the imaging unit 50 and the sample 12 so that all, or substantially all, of the sample 12 residing within the chamber 14 can be illuminated by the light source 18 and light transmitted through, or emanating from, the sample 12 can be acquired by the lens array 20. The present invention can be used with any positioning system that provides sufficient movement resolution; e.g., both fine movement for imaging and gross movement to establish, for example, an initial position of the sample.

As indicated above, the light source 18 can be configured to produce a light line that impinges on the sample 12 residing within the chamber 14. In such an embodiment, the positioning system 26 would be operative to create relative movement between the sample chamber 14 and the imaging unit 50 in a direction (referred to hereinafter as the "scanning direction") along the "Y" axis that is substantially perpendicular to the light line, and in some instances also in a direction along the "Z" direction as well. In some instances, a single pass of the light line across the sample 12 will permit the entire sample 12 to be imaged. In other instances, the positioning system 26 directs multiple passes of one or both of the imaging unit 50 and sample 12 relative to the other.

In addition to the movement in the scanning direction (i.e., the "Y" axis), some embodiments of the positioning system 26 are also operable to move one or both of the imaging unit 50 and the chamber 14 laterally (i.e., perpendicular to the scanning direction; the "X" axis) in defined increments to facilitate acquiring a desired image resolution. This embodiment is described in greater detail below.

The relative movement created by the positioning system 26 can be accomplished, for example, through the use of one or more stepper motors and associated mechanical linkage (e.g., gears, belts, etc.). The positioning system 26 can produce continuous and/or incremental motion of one or both of the imaging unit 50 and sample chamber 14. In some embodiments, the positioning system 26 is operable to move one or both of the sample 12 and the imaging unit 50 relative to each other to predetermined positions; e.g., in those instances where it is desirable to only image a portion of the sample 12. Positioning systems are well known in the art, and the present invention is not limited to any particular configuration thereof. For ease of description, the positioning system 26 shall be described hereinafter as being adapted to move the sample 12 relative to a fixed position imaging unit 50. The present invention, however, is not limited to this embodiment.

During operation of the staggered CIS, the light source 18 directs light toward the sample 12 to be imaged (i.e., the illuminated region). For purposes of providing an illustrative example, the light is described herein as a line of substantially continuous and uniform light beam (i.e., a "light line") that impinges on the sample 12. A light line is an example of a geometric form that the light can assume, and the present invention is not limited thereto. In a transmittance mode, the line of light passes through the sample 12 within the chamber 14 and impinges on the lens array 20. In a fluorescence mode, the line of light excites a fluorescent emission from a colorant admixed with the sample 12, which emission is at one or more wavelengths different than the wavelength(s) of the incident light. At least a portion of the emitted light impinges on the lens array 20. Each micro lens 30 within the lens array 20 receives, focuses, and directs the light emanating from the sample 12 toward an aligned CCD (or other element) disposed within the image detector 22. The image detector 22 generates a data signal based on the received light signal, which data signal is representative of the illuminated segment of the sample 12. The above description describes how a light line is applied and an image created at a given relative position of the imaging unit 50 and the sample 12. In most instances, however, the imaging process is dynamic.

The positioning system 26 moves the sample 12 in the scanning direction, relative to the imaging unit 50, thereby exposing the entire, or substantially the entire, sample 12 to the line of light over a given period of time. As the sample 12 is incrementally or continuously moved past the light line, data signals from the image detector 22 representative of the imaged sample 12 are sent to the processor and an image of the entire sample 12 is produced.

During the movement of the sample 12, the resolution field 42 of each micro lens 30 and the offset 44 between rows 31 permits the creation of an uninterrupted image in the lengthwise direction at any given widthwise position when all of the rows 31 of the array 20 are moved past the widthwise position in the scanning direction. The uninterrupted images at each widthwise position are then collectively summed to produce a high resolution image of the entire sample 12.

To illustrate, the system 10 will be described in terms of the lens array 20 embodiment diagrammatically shown in FIG. 6, which array 20 has the five rows (R1-R5), with each row 31 having eight (N=8) five micron (5μ) diameter micro lenses 30. Each micro lens 30 has a one micron (1μ) resolution field 42, and the lengthwise offset between rows 31 is one micron (1μ). The working distance is in the range of about 0.1 mm to 0.2 mm. The numerical aperture of the micro lenses 30 is about 0.33. In an alternative embodiment, a substantially higher resolution can be attained by using a lens array disposed at a working distance is 0.15 mm, and having a pitch of 50μ, and fifty rows.

As a particular segment 48 of the sample 12 is moved past each row 31 of the lens array 20, certain portions of the transmitted (or emitted) light are captured by an aligned micro lens 30 and image detector element(s) 37. For example, as the sample segment 48 moves past the first row (R1) of the lens array 20, the micro lens 30 and image detector elements 37 aligned with columnar portions 1, 6, 11, 16, 21, 26, 31, and 36 capture a one micron portion of the light transmitted through the sample segment 48. As the sample segment moves past the second row (R2) of the lens array 20, the micro lens 30 and image detector elements aligned with columnar portions 2, 7, 12, 17, 22, 27, 32, and 37 capture a one micron portion of the light transmitted through the sample segment 48. The process continues similarly until the sample segment 48 has passed all five rows (R1-R5) of the lens array 20, at which point light has been captured in all forty columnar portions extending widthwise across the sample 12. The aligned elements 37 of the image detector 22 produce signals representative of the captured light and those signals are subsequently processed to collectively produce an uninterrupted image (i.e., a "frame") of the sample segment 48 at a one micron resolution field 42. The process is repeated for each segment 48 of the sample 12 that is passed by the array 20, and the signals representative of the received light are processed to collectively produce a high resolution (e.g., one micron) image of the sample 12.

In an alternative embodiment, a smaller staggered lens array 20 can be used and high resolution still accomplished by utilizing movement of the sample 12 relative to the array 20 (or vice versa) in the scanning direction as described above, in combination with movement in a lateral direction (i.e., movement perpendicular to the scanning direction). For example, assume a lens array 20 has three (3) rows 31 of micro lenses 30, with each row 31 having eight (8) five micron (5μ) micro lenses 30, with each micro lens 30 having a one micron (1μ) resolution field 42. A sample segment 48 passed by the lens array 20 (or vice versa) in the manner described above relative to FIG. 6 would not capture sufficient columnar portions of light to produce an uninterrupted image of the sample segment 48; e.g., as shown in FIG. 7, after a first pass of a sample segment 48 by the lens array 20 and light source 18 (with the lens array 20/light source 18 held in an initial position), the micro lenses 30 and image detector elements aligned with columnar portions 1, 3, 5, 6, 8, 10, 11, 13, 15, 16, 18, 20, 21, 23, 25, 26, 28, 30, 31, 33, 35, 36, 38, and 40 each capture a one micron (1μ) columnar portion of the light transmitted through the sample segment 48. Shifting the sample 12 laterally by one micron (1μ) and passing the sample 12 by the lens array 20/light source 18 again enables the capture of those columnar portions of the transmitted light not captured in the first pass. The image portions from the two passes are subsequently combined to produce an uninterrupted image of the sample segment 48. All the transmitted light received from the segments 48 is subsequently processed to create an image having the same high resolution as that provided by the lens array 20 configuration shown in FIG. 6.

Figure 10:
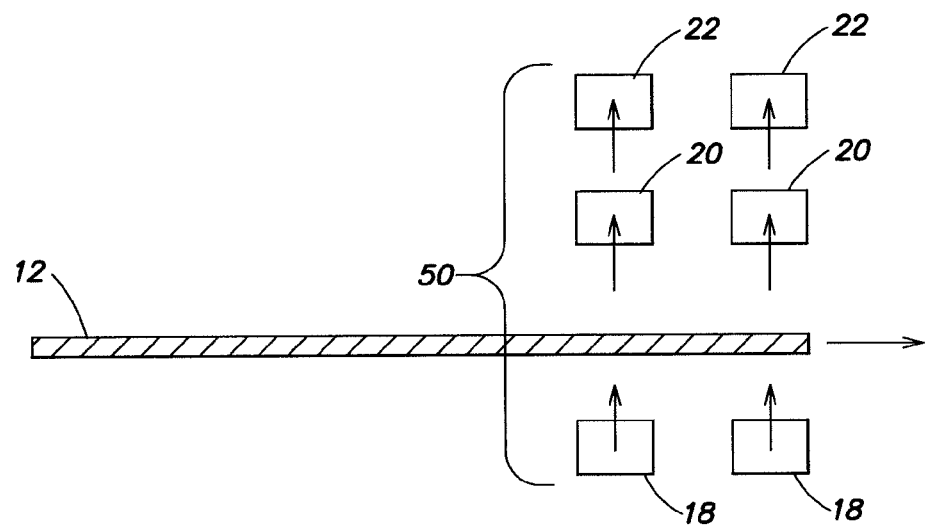
FIG. 10 is a diagrammatic illustration showing an embodiment of the present invention having a plurality of imaging units, shown relative to a sample.
Figure 11:
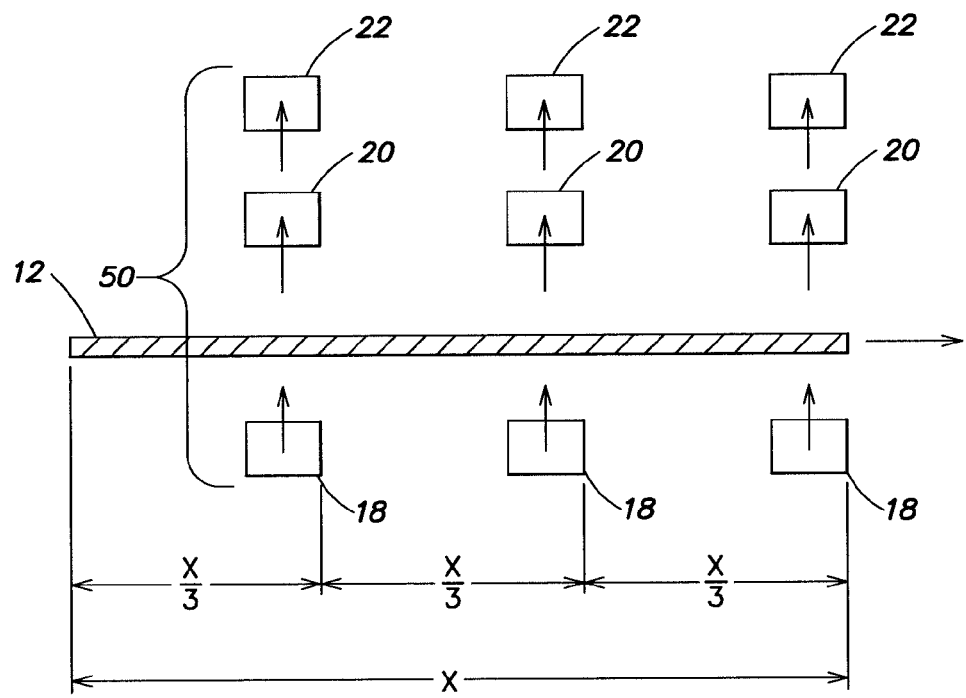
FIG. 11 is a diagrammatic illustration showing an embodiment of the present invention having a plurality of imaging units, shown uniformly spaced apart and disposed relative to a sample.

In some embodiments the present system 10 includes one or more additional imaging units 50. In the embodiment diagrammatically illustrated in FIG. 10, for example, two imaging units 50 are disposed relative to a planar sample 12. Each imaging unit 50 includes a light source 18 disposed on one side of the sample 12, and a lens array 20 and image detector 22 disposed on the opposite side of the sample 12. As indicated above, however, the present invention is not limited to these imaging unit 50 configurations. The multiple imaging units 50 can be configured to operate in a number of different ways to facilitate the present method. In some embodiments, for example, one of the imaging units 50 can be configured to image the sample 12 using light at a first set of wavelengths, and the other imaging unit 50 can be used to image the sample 12 at a second set of wavelengths (either "set" may include only a single wavelength). The first set of wavelengths is different from the second set of wavelengths. A single pass of the sample 12 relative to the imaging units 50 permits both units to image the sample 12 in a very short period of time. Alternatively, each imaging unit 50 could be aligned and configured to acquire a portion of the sample image (e.g., each imaging unit 50 is laterally offset from the other imaging unit 50) and the entire sample image collectively produced from the data acquired by each unit 50. The diagrammatic representation of FIG. 11 illustrates an embodiment wherein a sample 12 has a scanning distance length equal to "X", and each of the three imaging units 50 are uniformly spaced apart from one another by a distance of "X/3". In this embodiment, the entire scanning length of the sample 12 can be imaged by moving the sample 12 relative to the imaging units 50 (or vice versa) a distance equal to about "X/3". The entire sample image is collectively produced from the portion imaged by each imaging unit 50.

While various embodiments of the present invention have been disclosed, it will be apparent to those of ordinary skill in the art that many more embodiments and implementations are possible within the scope of the invention. Accordingly, the present invention is not to be restricted except in light of the attached claims and their equivalents.

What is claimed is:

1. An apparatus for imaging a biologic sample, comprising:
at least one light source adapted to selectively illuminate a region of the sample;
at least one lens array having a plurality of lengthwise extending rows, which rows are successively arranged in a widthwise direction, and each row having a plurality of micro lenses each having a resolution field, and each adapted to receive light from the illuminated region of the sample and to produce a beam of light wherein each row includes a first micro lens and the first micro lens in each successive row is offset from the first micro lens in the previous row by a predetermined amount extending in the lengthwise direction, wherein the offset between successive rows aligns the resolution fields of the plurality of micro lenses to collectively create a continuous resolution field across the length of the lens array;
at least one image detector adapted to receive light beams from the lens array and provide data signals representative of the received light beams;
a positioning system adapted to move the lens array and image detector relative to the sample, or vice versa, or both; and
an image processor adapted to produce an image signal indicative of the illuminated region of the sample produced from the data signals.

2. The apparatus of claim 1, wherein the positioning system is adapted to move the lens array, light source, and image detector relative to the sample, or vice versa, or some combination thereof.

3. The apparatus of claim 1, wherein each first micro lens is offset by an amount between about one half the resolution field of the micro lenses to about twice the resolution field of the micro lenses.

4. The apparatus of claim 1, wherein the resolution field of each micro lens within the array has a resolution field of "n" microns.

5. The apparatus of claim 4, wherein the offset between rows is substantially equal to "n" microns.

6. The apparatus of claim 1, wherein the image detector comprises a number of image detector elements that is equal to the number of micro lenses within the lens array.

7. The apparatus of claim 6, wherein each micro lens is aligned with one of the image detector elements.

8. The apparatus of claim 1, wherein the image detector comprises a number of image detector elements that is greater than the number of micro lenses within the lens array.

9. The apparatus of claim 8, wherein the micro lenses each have a resolution field of about one micron, and the apparatus is operable with a working distance in the range of about 0.1 mm to 0.2 mm.

10. The apparatus of claim 1, wherein the positioning system is adapted to move the light source and lens array relative to the sample, or vice versa, along a single direction to create the continuous resolution field across the length of the lens array.

11. The apparatus of claim 1, wherein the positioning system is adapted to move the light source and lens array relative to the sample, or vice versa, along a plurality of directions to create the continuous resolution field across the length of the lens array.

12. The apparatus of claim 1, further comprising a plurality of imaging units, each unit including one of the light sources, one of the lens arrays, and one of the image detectors; and
wherein each imaging unit is positioned apart from the other imaging units; and wherein the positioning system is adapted to move each imaging system relative to the sample, or vice versa, or both.

13. An apparatus for imaging a biologic sample, comprising:
at least one light source adapted to selectively illuminate a region of the sample;
at least one lens array having a plurality of lengthwise extending rows, which rows are successively arranged in a widthwise direction, and each row having a plurality of micro lenses each having a resolution field and each adapted to receive light from the illuminated region of the sample and to produce a beam of light wherein each row includes a first micro lens and the first micro lens in each successive row is offset from the first micro lens in the previous row by a predetermined amount extending in the lengthwise direction, wherein the offset between successive rows aligns the resolution fields of the plurality of micro lenses to collectively create a continuous resolution field across the length of the lens array;
at least one image detector adapted to receive light beams from the lens array and provide data signals representative of the received light beams;
a positioning system adapted to move the lens array and image detector relative to the sample, or vice versa, or both; and
an image processor adapted to produce an image signal indicative of the illuminated region of the sample produced from the data signals;
a plurality of imaging units, each unit including one of the light sources, one of the lens arrays, and one of the image detectors;
wherein each imaging unit is positioned apart from the other imaging units; and
wherein the positioning system is adapted to move each imaging system relative to the sample, or vice versa, or both; and
wherein the apparatus is operable to scan a distance "x" of the sample, and the plurality of imaging units includes "y" integer number of imaging units, and the imaging units are spaced apart from adjacent imaging units by a distance substantially equal to 1/y*x.

14. A staggered lens array, comprising:
a plurality of lengthwise extending rows, which rows are successively arranged in a widthwise direction, and each row having a plurality of micro lenses each having a resolution field of "n" microns, and each adapted to receive light and produce a beam of light, wherein each row includes a first lens and the first lens in each successive row is offset from the first lens in the previous row by a predetermined amount extending in the lengthwise direction;
wherein the offset between successive rows aligns the resolution fields of the plurality of micro lenses to collectively create a continuous resolution field across the length of the lens array.

15. A method of imaging a sample, comprising the steps of:
providing an imaging unit having a light source, a lens array, and an image detector, wherein the lens array has a width, a length, and a plurality of lengthwise extending rows, which rows are successively arranged in a widthwise direction, and each row having a plurality of micro lenses each having a resolution field, and each adapted to receive light and produce a beam of light, wherein each row includes a first micro lens and the first micro lens in each successive row is offset from the first micro lens in the previous row by a predetermined amount extending in the lengthwise direction;
selectively illuminating the sample, such that light exiting the sample is received by the lens array and passed to the image detector, which image detector produces data signals representative of the sample from the received light;
moving one or both of the imaging unit and sample relative to the other such that substantially all of the sample is illuminated; and
processing the data signals to produce an image of the sample.

16. The method of claim 15, wherein the offset between successive rows aligns the resolution fields of the plurality of micro lenses to collectively create a continuous resolution field across the length of the lens array.

17. The method of claim 15, wherein the light received by the lens array is transmitted through the sample.

18. The method of claim 15, wherein the light received by the lens array is emitted from a colorant excited within the sample by the illuminating light.

19. The method of claim 15, wherein the predetermined amount of offset is between about one half the resolution field of the micro lenses to about twice the resolution field of the micro lenses.

20. The method of claim 15, wherein the resolution field of each micro lens within the array has a resolution field of "n" microns, and the offset between rows is substantially equal to "n" microns.

21. The method of claim 15, including the step of operating the imaging unit such that the lens array and the sample have a working distance in the range of about 0.1 mm to 0.2 mm.

22. The method of claim 15, wherein the moving step includes moving the light source and lens array relative to the sample, or vice versa, along a single direction to create the continuous resolution field across the length of the lens array.

23. The method of claim 15, wherein the moving step includes moving the light source and lens array relative to the sample, or vice versa, along a plurality of directions to create the continuous resolution field across the length of the lens array.

* * * * *